US012582597B2

(12) United States Patent (10) Patent No.: US 12,582,597 B2

Conti et al. (45) Date of Patent: Mar. 24, 2026

(54) WAX OF NATURAL ORIGIN FOR COSMETIC PRODUCTS

(71) Applicant: BRASCA INDUSTRIAL SRL, Milan (IT)

(72) Inventors: Simone Conti, Milan (IT); Federico Piva, Milan (IT)

(73) Assignee: ROELMI HPC S.R.L., Origgio (IT)

( * ) Notice: Subject to any disclaimer, the term of this patent is extended or adjusted under 35 U.S.C. 154(b) by 427 days.

(21) Appl. No.: 18/312,624

(22) Filed: May 5, 2023

(65) Prior Publication Data

US 2023/0355504 A1 Nov. 9, 2023

(30) Foreign Application Priority Data

May 5, 2022 (IT) ........................ 102022000009239

(51) Int. Cl.
A61K 8/92 (2006.01)
A61Q 1/06 (2006.01)

(52) U.S. Cl.
CPC ................ A61K 8/922 (2013.01); A61Q 1/06 (2013.01); *A61K 2800/30* (2013.01); *A61K 2800/805* (2013.01)

(58) Field of Classification Search
None
See application file for complete search history.

(56) References Cited

U.S. PATENT DOCUMENTS

| | | | | |
|---|---|---|---|---|
| 11,986,550 B1 * | 5/2024 | Lushka | .................... | A61K 8/06 |
| 2019/0388333 A1 | 12/2019 | Zewuhn et al. | | |
| 2021/0169771 A1 | 6/2021 | Schecker et al. | | |

OTHER PUBLICATIONS

Search Report and written opinion of Priority Application IT 202200009239 issued Dec. 1, 2022.

* cited by examiner

*Primary Examiner* — Danah Al-Awadi
(74) *Attorney, Agent, or Firm* — Silvia Salvadori, P.C.; Silvia Salvadori

(57) ABSTRACT

The invention relates to a wax of natural origin for cosmetic products consisting of a homogeneous phase of *Helianthus annuus* sunflower seed wax wherein hydrogenated castor oil is contained. The wax is obtained quickly cooling a molten solution obtained melting separately and then mixing together the aforesaid molten constituents in suitable ratios. The natural origin wax of the invention gives to the cosmetic products containing it useful properties in terms of stability and retains the same flowability of products containing plastic polymers such as polyethylene.

11 Claims, 2 Drawing Sheets

Figure 1

WAX OF NATURAL ORIGIN FOR COSMETIC PRODUCTS

This application claims priority to and the benefit of Italian Patent Application no. 102022000009239 filed May 5, 2022, the content of which is incorporated herein by reference in its entirety.

An object of the present invention is a wax of natural origin consisting of a homogeneous phase of *Helianthus annuus* sunflower seed wax wherein hydrogenated castor oil is contained, useful for the formulation of cosmetic products. Other aspects of the invention relate to a process for preparing the wax and to cosmetic products containing it as a functional substitute of plastic polymers such as polyethylene, in particular stick or non-stick products for colour cosmetics.

BACKGROUND OF THE INVENTION

"Colour cosmetics" is a term that refers to different categories of products for the makeup of various body parts, such as skin, cheeks, eyes, and lips, used to improve the general physical aspect, hide defects, or define characteristics.

Beside powdered cosmetic products such as face powders and lipstick, and cream products, such as day creams and cream based on emulsions, the more used colour cosmetics comprise lipsticks. These are generally consisting of a wax matrix wherein liquid and semisolid oils are incorporated, besides pigments and fillers. They are in the form of solid stick and are useful not only for enhancing the lips colour but also for protecting and taking care of them.

One of the main drawbacks of the cosmetic products in the form of a stick is that they often contain polyethylene or plastic materials needed to facilitate the manufacturing process and guarantee the product stability and the performance thereof, in particular the flowability, on the application surfaces, for example lips. Thus, the use of plastic materials or polyethylene is perceived as less and less favorably by consumers preferring cosmetic products containing eco-friendly and sustainable materials and showing fewer potential risks for the environment.

Therefore, it is important to individuate ingredients of natural origin which can be used as substitutes for plastic materials such as polyethylene and other products of synthetic origin for the production of stable colour cosmetics, both in the stick and non-stick form.

US 2021/0169771 A1 describes a preparation for lip care containing a wax mixture of a) castor oil wax (INCI name: hydrogenated castor oil), b) sunflower wax (INCI name *Helianthus annuus* seed wax), c) beeswax (INCI name: Alba wax), besides other ingredients commonly used for this kind of preparations. Preferably, components a) and b) are present in the preparation in concentrations of 2-10% by weight, while component c) is present in concentrations of 5-20% by weight, in relation to the total weight of the preparation. The preparation is obtained melting a mixture of components a), b) and c) to which the other ingredients commonly used in preparations for lip care are added later. The mixture is melted in a casting annulus kept at a temperature 5-15° C. higher than the melting temperature of the mixture and then cooled at 6-25° C. until solid. The solid mass, shaped in stick form, is then expelled shaped and placed in suitable containers.

DESCRIPTION OF THE FIGURES

FIG. 1 DSC patterns of the wax of natural origin of the invention and of the single components thereof.

DESCRIPTION OF THE INVENTION

Figure 2:
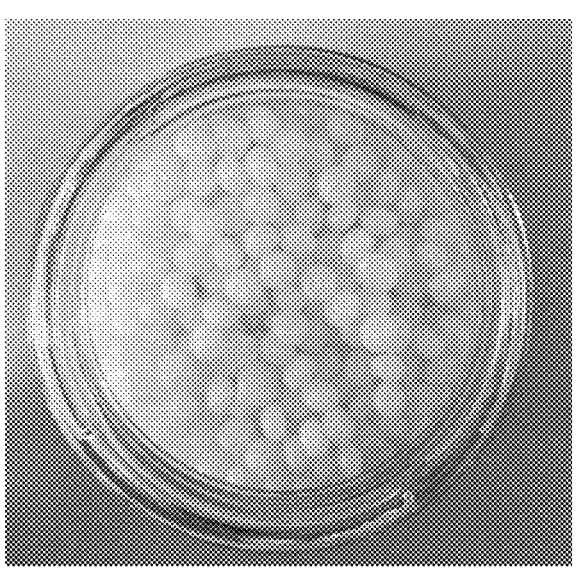
FIG. 2 Photography of the wax of natural origin of the invention obtained in the form of homogeneous drops.

It has been found now that, quickly cooling a molten solution obtained combining in suitable proportions *Helianthus annuus* sunflower seed wax and hydrogenated castor oil molten separately, a homogeneous phase in the form of beads or flakes is obtained, consisting of a sunflower seed wax matrix wherein hydrogenated castor oil is contained. Said homogeneous phase, when used for the preparation of cosmetic products, provides useful properties in terms of stability, keeping the same flowability of products containing plastic polymers, in particular polyethylene.

Therefore, object of the present invention is a wax of natural origin for cosmetic use consisting of a homogeneous phase of *Helianthus annuus* sunflower seed wax wherein hydrogenated castor oil is contained, said wax containing 10-30% by weight of hydrogenated castor oil and 70-90% by weight of *Helianthus annuus* sunflower seed wax.

Preferably, the hydrogenated castor oil is present in an amount between 15 and 30% by weight relative to the mixture of the two components.

Preferably, the *Helianthus annuus* sunflower seed wax is present in an amount between 70 and 85% by weight relative to the mixture of the two components.

Preferably, the weight ratio between the hydrogenated castor oil and the *Helianthus annuus* sunflower seed wax is between 1:9 and 3:7.

The hydrogenated castor oil and the sunflower seed wax can be prepared with known methods and they are commercially available products.

Figure 1:
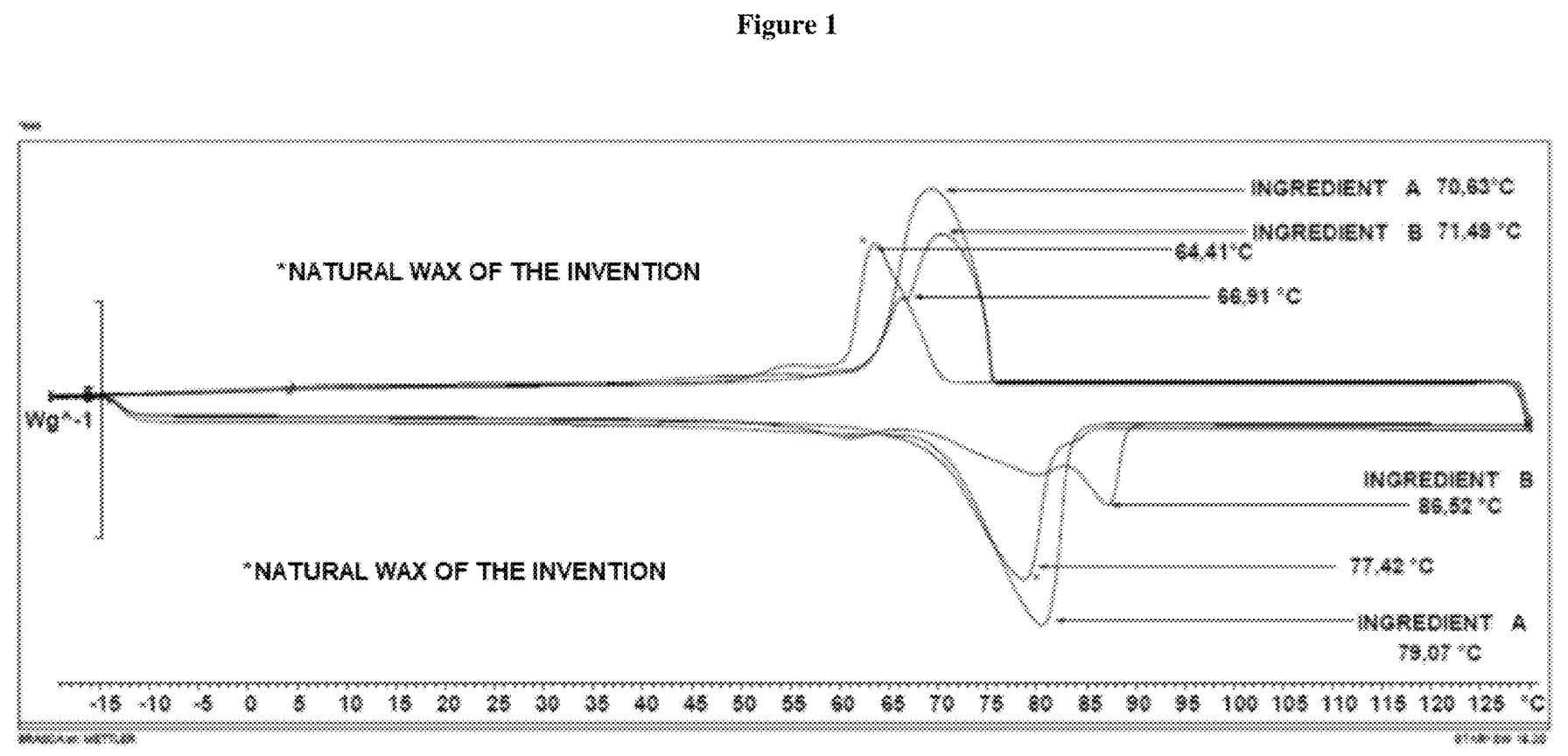

The wax of the invention appears as a homogeneous solid in pearls, being its properties different from those of the single raw materials, as results from the comparison of the DSC patterns of the wax of the invention and components thereof shown in FIG. 1 and discussed in Example 1.

The wax of the invention is obtained by a method comprising the following steps and representing a further object of the invention:

a) heating under stirring the *Helianthus annuus* sunflower seed wax up at a temperature ranging from 80° C. to 100° C., until complete melting of the wax;

b) heating under stirring the hydrogenated castor oil up to a temperature ranging from 90° C. to 110° C., until complete melting of the wax;

c) mixing under stirring the waxes obtained from steps a) and b), keeping a temperature from 95° C. to 125° C., preferably for a time comprised between 15 minutes and 30 minutes, until complete homogenization of the solution;

d) cooling down the solution obtained in step c) at a temperature ranging from 5° C. to 15° C. for a maximum time of 15 minutes, preferably up to 5 minutes, in order to obtain a homogeneous phase consisting of *Helianthus annuus* sunflower seed wax matrix wherein the hydrogenated castor oil is solubilized;

e) keeping at room temperature the homogeneous phase obtained in step d), preferably for at least 15 minutes, until obtaining said wax.

In an embodiment of the invention, once at the end of step c) the complete homogenization of the solution is obtained, the subsequent processing through thermal shock at the tableting machine is performed (step d), preferably by dropping, o in a flaker apparatus, in order to obtain an immediate transformation from liquid product to a final form which preferably is in the form of homogeneous drops or flakes.

According to this embodiment of the invention, the solution obtained in step c) is transported to the tableting and flaking plant (flaker) by a pipeline system heated by furnaces at a controlled temperature from 95° C. to 125° C. The product is fed at a controlled temperature on a roller rotor, the edge of which is designed with teeth of regular shape and pitch. The liquid product slips steadily among the teeth; the drops accumulate on the back of each tooth, due to the complementary comb in contact with the toothed rotor. In step d), the drops are then deposed on the steel belt cooled at a controlled temperature between 5° C. and 15° C. by a chilling machine (chiller) in a closed loop, due to the centrifugal and gravitational force, generating simultaneously the drop form. The rotation speed of the rotor is synchronized with that of the steel belt in order to obtain a homogeneous shape of the tablets or flakes. FIG. 2 shows a photography of the wax of the invention obtained in the form of homogeneous drops.

The wax of the invention can be used in the formulation of cosmetic products as structuring agent, suspending agent, or rheological modifier instead of polyethylene, allowing performances better or comparable to those of the sunflower seed wax and the hydrogenated castor oil, with the further advantage of substituting the polyethylene with products of natural origin showing fewer potential risks for the environment.

Therefore, a further object of the invention is a cosmetic product containing the wax as above defined and obtained by the above described process as structuring agent, suspending agent, or rheological modifier.

The main applications of the wax of natural origin of the invention relate to:

stick products for colour cosmetics (anhydrous formulations) wherein it can be used in percentages of 0.5-20% by weight relative to the formulation, and wherein it acts as a structuring agent and rheological modifier of oils, like polyethylene;

non-stick products for colour cosmetics, for example anhydrous concealers, wherein it can be used in percentages of 0.5-18% by weight relative to the formulation, playing the functions of structuring agent and suspending agent. As demonstrated in Example 6, the polyethylene does not allow to formulate a stable anhydrous concealer and provides a lower performance in terms of suspending capacity than the wax of the invention.

In a preferred embodiment the cosmetic product containing the wax of the invention is in stick form.

In addition to the wax of the invention, the aforesaid cosmetic products contain other ingredients typically used for their preparation such as oils and/or triglycerides, alcohols, UV filters, pigments, perfumes and/or flavors.

In a preferred embodiment the cosmetic product does not contain polyethylene, which is replaced by the wax of the invention. The latter exerts the same functions of polyethylene in a more advantageous way, as will be evident from the following Examples.

Example 1—Preparation of the Wax of Natural Origin of the Invention

| Ingredient | INCI NAME | CAS NUMBER | EINECS NUMBER |
|---|---|---|---|
| A | *HELIANTHUS ANNUUS* SEED WAX (ABWAX SUNFLOWER PEARLS ™) | 68937-99-5 | 232-273-9 |
| B | Hydrogenated Castor Oil (ABWAX CASTOR WAX ™) | 8001-78-3 | 232-292-2 |

The wax of the invention is obtained by the following process:

1. Heating under stirring Ingredient A up to a temperature of 100° C. until complete melting of the wax.
2. Heating under stirring Ingredient B up to a temperature of 100° C. until complete melting.
3. Mixing 85% parts by weight of A with 15% parts by weight of B under stirring keeping a temperature of 95° C. for 5 minutes until complete homogenization of the solution.
4. Cooling down the system within 2 minutes at a temperature of 5° C. in order to obtain a continuous phase consisting of Ingredient A wherein Ingredient B is dispersed.
5. Keeping the system at rest for 15 minutes.

The obtained product appears as a homogeneous bead (FIG. 2) showing DSC set in FIG. 1, in comparison with DSCs of Components A and B.

The thermal profile is so composed:

At the bottom of FIG. 1 the heating curve is reported wherein the melting temperatures of the *Helianthus annuus* sunflower seed wax (Ingredient A), the hydrogenated castor oil (Ingredient B), and the wax of the invention can be identified. The pattern of the wax of the invention shows a peak at 10.5 minutes which is absent in pattern A. This peak can be associated to the presence of Ingredient B which is integrated in the wax of the invention. This causes the non-overlapping of the two curves.

This difference may be noted in the upper part of the thermal profile of the substances wherein the cooling curves appear. From these curves it is possible to extrapolate the crystallization temperatures. The wax curve does not overlap with Ingredient A. The presence of a second peak at 6.5 minutes is linked to the presence of Ingredient B in the wax of the invention.

The drop point is the specific temperature of a material wherein a drop of the liquefied substance flows out thanks to gravity through a metal mold hole having standard dimensions. Therefore, the drop point represents a thermal parameter having a direct impact on product applications.

The drop point measurement, performed with the Drop Point instrument (Mettler Toledo) wherein a heating speed of 1° C./min and a start temperature of 50° C. are set, provides the following values.

| INGREDIENT | Drop Point |
|---|---|
| INGREDIENT A | 80 +/− 2° C. |
| INGREDIENT B | 87 +/− 2° C. |
| WAX OF THE INVENTION | 84 +/− 2° C. |

5

Example 2—Formulation and Stability of an Anhydrous Concealer

Using the production method below three anhydrous concealers are prepared having the formula set in Table 1, wherein the entry "INGREDIENT" indicates alternatively *Helianthus annuus* seed wax, hydrogenated castor oil, or the wax of the invention, and percentages are referred to the total weight of the formulation.

TABLE 1

| Phase | NCI name | Trade name | % |
|---|---|---|---|
| 1 | Isodecyl Neopentanoate | Neolight 100P | 26.40 |
| | | INGREDIENT | 7.00 |
| | Diisostearyl Malate | Haimalate DIS | 20.00 |
| 2 | Titanium Dioxide (and) Isopropyl Titanium Triisostearate | BTD-401 | 5.60 |
| | CI 77491 (and) Isopropyl Titanium Triisostearate | BRO-12 | 0.15 |
| | CI 77499 (and) Isopropyl Titanium Triisostearate | BBO-12 | 0.05 |
| | CI 77492 (and) Isopropyl Titanium Triisostearate | BYO-12 | 1.00 |
| | Isododecane | Isododecane | 29.80 |
| | Silica | MSS-500/N | 10.00 |

Production Method

Phase 1 is weighted and molten up to 85+/−5° C. under magnetic stirring.

Phase 2 is weighted separately.

Phase 2 is added to Phase 1. The mixture is homogenized by a laboratory homogenizer.

The mixture is heated up to 87+/−5° C. and casted in a previously heated concealer mold.

The mold is allowed to cool at room temperature for 10 minutes and then at −20° C. for 10 minutes.

The solid sticks are then delivered into a suitable packaging.

A stability study of the three obtained formulations shows that only the formulation containing the wax of the invention is stable after 6 months in oven at 40° C., while the formulations containing *Helianthus annuus* seed wax or hydrogenated castor oil are instable after 5 days at 40° C. The wax of the invention remains stable and homogeneous and does not become liquid.

| INGREDIENT | Formulation Number |
|---|---|
| Wax of the invention | 1 |
| *Helianthus annuus* seed wax | 2 |
| Hydrogenated castor oil | 3 |

Example 3—Formulation of Lipsticks and Colour Release Thereof

Two lipsticks were prepared having the formula set in Table 2 wherein the entry "INGREDIENT" indicates:

The wax of the invention; or

A wax obtained adding in portions and mixing *Helianthus annuus* seeds and hydrogenated castor oil;

and the percentages are referred to the total weight of the formulation.

The preparation method is the following:

Phase 1 is weighted and molten up to 85+/−5° C. under magnetic stirring.

Phase 2 is weighted separately.

6

An aliquot (25+/−5%) of Phase 1 is withdrawn and poured in Phase 2 and stirred until obtaining a homogeneous dispersion.

Once cooled at 25° C., the dispersion becomes semisolid and is further homogenized to the three roll mill until the pigment is completely dispersed. The mixture is then added to the remaining portion of Phase 1 until complete melting.

The system is heated up to 88+/−3° C. and poured in a 60° C. previously heated lipstick mold.

The mold is allowed to cool at room temperature for 10 minutes and then at −20° C. for 10 minutes.

The solid sticks are then inserted into a suitable packaging.

TABLE 2

| Phase | INCI NAME | % |
|---|---|---|
| 1 | Tripelargonin | 34.9 |
| | Castor Oil | 20 |
| | Polyglyceryl-2 Isostearate/Dimer Dilinoleate Copolymer | 10 |
| | C10-18 Triglycerides | 5 |
| | INGREDIENT | 15 |
| 2 | Red 7 | 15 |
| | o-cymen-5-ol | 0.1 |

A panel test carried out on 15 candidates showed that the product containing the wax of the invention provides a better colour release.

Example 4—Preparation and Base Performances for Stick

Two colorless stick bases were prepared having the formula set in Table 3, wherein the term "WAX" indicates alternatively polyethylene or the wax of the invention and the percentages are referred to the total weight of the formulation.

The preparation method is the following. All components are weighted and the system is heated up to 90+/−3° C. under magnetic stirring. Once a homogeneous solution is formed, the melted lipbalm is poured in a 60° C. previously heated mold. The mold is allowed to cool at room temperature for 10 minutes and then at −20° C. for 10 minutes. The solid sticks are then delivered into a suitable packaging.

TABLE 3

| Trade name | INCI name | % |
|---|---|---|
| WAX | — | 12 |
| Emotion Light | Tripelargonin | 78 |
| Olifeel Pearls | C10-18 Triglycerides | 10 |

The hardness and consistency analysis was performed subjecting samples to irreversible deformation by the penetration of a cone-shaped probe. The greatest the depth the probe reaches, the lowest is the hardness. Both formulations show the same penetration value (dmm) of 60-75 mm*$10^{-1}$.

A panel test was carried out on 15 candidates, wherein the formulation with the wax of the invention resulted slightly more flowable compared to the one obtained with polyethylene. Therefore, the use of the wax of the invention allows to obtain a more flowable, and consequently more pleasant stick base when placed on skin or lips.

Example 5—Lipstick Formulation

Two lipsticks having the formula set in Table 4 were prepared wherein the term "WAX" indicates polyethylene or the wax of the invention and the percentages are referred to the total weight of the formulation. The chemical-physical and applicative performances thereof were assessed.

The preparation method is the following.

Phase 1 is weighted and molten up to 85+/−5° C. under magnetic stirring.

Phase 2 is weighted separately.

Phase 2 is added to Phase 1. The mixture is homogenized by a laboratory homogenizer.

The mixture is heated up to 87+/−5° C. and casted in a 60° C. previously heated lipstick mold.

The mold is allowed to cool at room temperature for 10 minutes and then at −20° C. for 10 minutes.

The solid sticks are then delivered into a suitable packaging

TABLE 4

| Phase | INCI name | Trade name | % |
|---|---|---|---|
| 1 | Tripelargonin | Emotion Light | 38.00 |
| | Hexyl Laurate | KAK HL | 15.00 |
| | *Simmondsia Chinensis* Seed Oil | Amioil jojoba | 9.50 |
| | WAX | | |
| | Oryza Sativa wax. Rhus Succedanea Fruit wax. Squalene. Shorea Robusta Resin | ABWAX Mimic Beeswax | 4.00 |
| | o-cymen-5-ol | Bioscontrol Element IM | 0.10 |
| | Butyrospermum Parkii Butter | Refined Amibutter Shea | 3.60 |
| 2 | CI 15850. Stearoyl Glutamic Acid. Polyhydroxystearic Acid | RED 6BA C-ASGP7 | 17.00 |
| | Silica | MSS-500/3H | 3.80 |

For both formulations the melting point is 61-67° C. and the drop point is 66-72° C.

A panel test showed that there is no difference in terms of stick hardness and colour release.

Example 6—Suspending Capacity Test

Tests were performed to assess the suspending capacity of the wax of the invention in comparison to polyethylene using the following formulations, wherein the percentages are referred to the total weight of the formulation.

Sample 1

| | |
|---|---|
| Polyethylene | 1% |
| Caprylic Capric Triglycerides | 98.8% |
| pearlscent pigment | 0.2% |

Sample 2

| | |
|---|---|
| Wax of the invention | 1% |
| Caprylic Capric Triglycerides | 98.8% |
| pearlscent pigment | 0.2% |

The preparation method is the following. The formulation components are weighted, the system is heated up to 87+/−5° C. under stirring until the formation of a dispersion. The dispersion is mixed in a laboratory homogenizer for five minutes.

It is then cooled at room temperature under stirring.

Sample stability was assessed for six months at 40° C.

After one week, Sample 1 containing polyethylene shows a precipitation of the pearlscent pigment, thus indicating the lower stability of the product. On the other hand, Sample 2 is homogeneous and more structured and keeps the pearlscent pigment suspended until six months.

The invention claimed is:

1. Method to produce a wax of natural origin for cosmetic use, wherein said wax consists of 70-90% by weight of *Helianthus annuus* sunflower seed wax and 10-30% of hydrogenated castor oil wherein the *Helianthus annuus* sunflower seed wax and the hydrogenated castor oil form a homogenous phase, said method comprising the following steps:
   a) heating under stirring the *Helianthus annuus* sunflower seed wax up at a temperature ranging from 80° C. to 100° C., until complete melting of the wax;
   b) heating under stirring the hydrogenated castor oil up at a temperature ranging from 90° C. to 110° C., until complete melting of the wax;
   c) mixing under stirring the molten waxes obtained from steps a) and b), keeping a temperature from 95° C. to 125° C., until complete homogenization of the solution;
   d) cooling down the solution obtained in step c) at a temperature ranging from 5° C. and 15° C. for a maximum time of 15 minutes in order to obtain a homogeneous phase consisting of *Helianthus annuus* sunflower seed wax matrix wherein the hydrogenated castor oil is dispersed;
   e) keeping at room temperature the homogeneous phase obtained in step d), until a wax is obtained.

2. Method according to claim 1, wherein:
   i) in step c) the mixing takes place in a time ranging from 15 minutes to 30 minutes;
   and, independently
   ii) in step e) the homogeneous phase is allowed to rest for at least 15 minutes.

3. Method according to claim 1, wherein in step d) the cooling takes place by dropping on a metallic surface, and the thus obtained homogeneous phase is in the form of pearls or flakes.

4. Method according to claim 3, wherein the cooling is obtained by a tableting machine or a flaker apparatus.

5. Wax for cosmetic use obtainable by the method according to claim 1.

6. Wax according to claim 5, consisting of 70-90% by weight of *Helianthus annuus* sunflower seed wax and 10-30% by weight of hydrogenated castor oil, wherein the *Helianthus annuus* sunflower seed wax and the hydrogenated castor oil form a homogeneous phase.

7. Cosmetic product containing the wax of claim 5 as a structuring agent, suspending agent, or rheological modifier.

8. Cosmetic product according to claim 7, in the form of a stick.

9. Cosmetic product according to claim 8, which is a lipstick.

10. The cosmetic product according to claim 7, wherein said cosmetic product does not contain polyethylene and said wax is used in place of polyethylene.

11. The method according to claim 1, wherein in step d) the cooling step occurs for a maximum time of up to 5 minutes.

* * * * *